United States Patent [19]

Morley et al.

[11] Patent Number: 5,412,095

[45] Date of Patent: * May 2, 1995

[54] TERAZOSIN MONOHYDROCHLORIDE AND PROCESSES AND INTERMEDIATE FOR ITS PRODUCTION

[75] Inventors: James A. Morley, Gurnee; John F. Bauer, Lake Bluff; Ramesh F. Patel, Chicago; Rodger E. Henry, Waukegan; Stephen G. Spanton, Grayslake, all of Ill.

[73] Assignee: Abbott Laboratories, Abbott Park, Ill.

[*] Notice: The portion of the term of this patent subsequent to Mar. 15, 2011 has been disclaimed.

[21] Appl. No.: 246,526

[22] Filed: May 20, 1994

Related U.S. Application Data

[63] Continuation-in-part of Ser. No. 178,184, Jan. 6, 1994, Pat. No. 5,362,730, which is a continuation-in-part of Ser. No. 90,721, Jul. 13, 1993, Pat. No. 5,294,615, which is a continuation-in-part of Ser. No. 54,917, Apr. 29, 1993, abandoned.

[51] Int. Cl.$^6$ .................. A61K 31/505; C07D 239/84
[52] U.S. Cl. .................................................... 544/291
[58] Field of Search ......................................... 544/291

[56] References Cited

U.S. PATENT DOCUMENTS

| | | | |
|---|---|---|---|
| 4,026,894 | 5/1977 | Winn et al. | 544/291 |
| 4,112,097 | 9/1978 | Winn et al. | 544/291 |
| 4,251,532 | 2/1981 | Roteman | 544/291 |
| 4,816,455 | 3/1989 | Schickanedev et al. | 514/254 |
| 5,212,176 | 5/1993 | Kyncl et al. | 544/291 |
| 5,294,615 | 3/1994 | Meyer et al. | 544/291 |

FOREIGN PATENT DOCUMENTS 5-78352  3/1993  Japan .

OTHER PUBLICATIONS

*Chem. Abstr.*, 119:95556y (1993).

*Primary Examiner*—Cecilia Tsang
*Attorney, Agent, or Firm*—Jerry F. Janssen

[57] ABSTRACT

The present invention provides a non-solvated crystalline polymorph of terazosin monohydrochloride designated Form III and methods for its preparation. Also disclosed is terazosin monohydrochloride methanolate and processes for its production as well as processes for its conversion to other crystalline forms of terazosin monohydrochloride.

2 Claims, 20 Drawing Sheets

TERAZOSIN MONOHYDROCHLORIDE AND PROCESSES AND INTERMEDIATE FOR ITS PRODUCTION

CROSS-REFERENCE TO RELATED APPLICATIONS

This application is a continuation-in-part of application Ser. No. 08/178,184 filed Jan. 6, 1994 now U.S. Pat. 5,362,730 which is a continuation-in-part of application Ser. No. 08/090,721 filed Jul. 13, 1993, now U.S. Pat. No. 5,294,615, issued Mar. 15, 1994 which, in turn, is a continuation-in-part of application Ser. No. 08/054,917 filed Apr. 29, 1993, now abandoned.

TECHNICAL FIELD

This invention relates to compounds having therapeutic utility and to chemical methods for their preparation. More particularly, the present invention concerns the compound 1-(4-amino-6,7-dimethoxy-2-quinazolinyl)-4-(tetrahydro-2-furoyl)piperazine monohydrochloride in a novel non-solvated crystalline polymorph, to chemical methods for its preparation, and to 1-(4-amino-6,7-dimethoxy-2-quinazolinyl)-4-(tetrahydro-2-furoyl)piperazine monohydrochloride methanolate and methods for its use as an intermediate for the preparation of non-solvated crystalline modifications of terazosin monohydrochloride.

BACKGROUND OF THE INVENTION

The compound 1-(4-amino-6,7-dimethoxy-2-quinazolinyl)-4-( tetrahydro-2furoyl)piperazine is known by the common name "terazosin." Terazosin is known to have utility for the treatment of hypertension, benign prostatic hyperplasia, and congestive heart failure. The compound and methods for its preparation are disclosed in U.S. Pat. No. 4,026,894. This patent discloses, in Example VI, a method of preparing terazosin which produces a non-solvated crystalline polymorph of the compound which, for the sake of identification, is termed crystalline "Form I" of the compound throughout this specification and the appended claims.

Pharmaceutical compositions comprising terazosin or a pharmaceutically acceptable salt are claimed in U.S. Pat. No. 4,112,097 together with their therapeutic use for the treatment of hypertension.

The dihydrate crystalline form of the hydrochloride salt of terazosin is marketed under the trade name Hytrin® and is the subject of U.S. Pat. No. 4,251,532.

The R(+)-enantiomer of terazosin is disclosed and claimed in U.S. Pat. No. 5,212,176, together with pharmaceutical compositions comprising the R(+)-enantiomer, and methods for the use of the compounds and its compositions for the treatment of hypertension, hyperinsulinemia, congestive heart failure, and benign prostatic hyperplasia.

U.S. Pat. No. 5,294,615 discloses a non-solvated crystalline polymorph of terazosin hydrochloride which is distinct from Form I referred to above and, for the sake of identification, is designated in that patent and in this specification and the appended claims as crystalline "Form II."

SUMMARY OF THE INVENTION

Figure 1A:
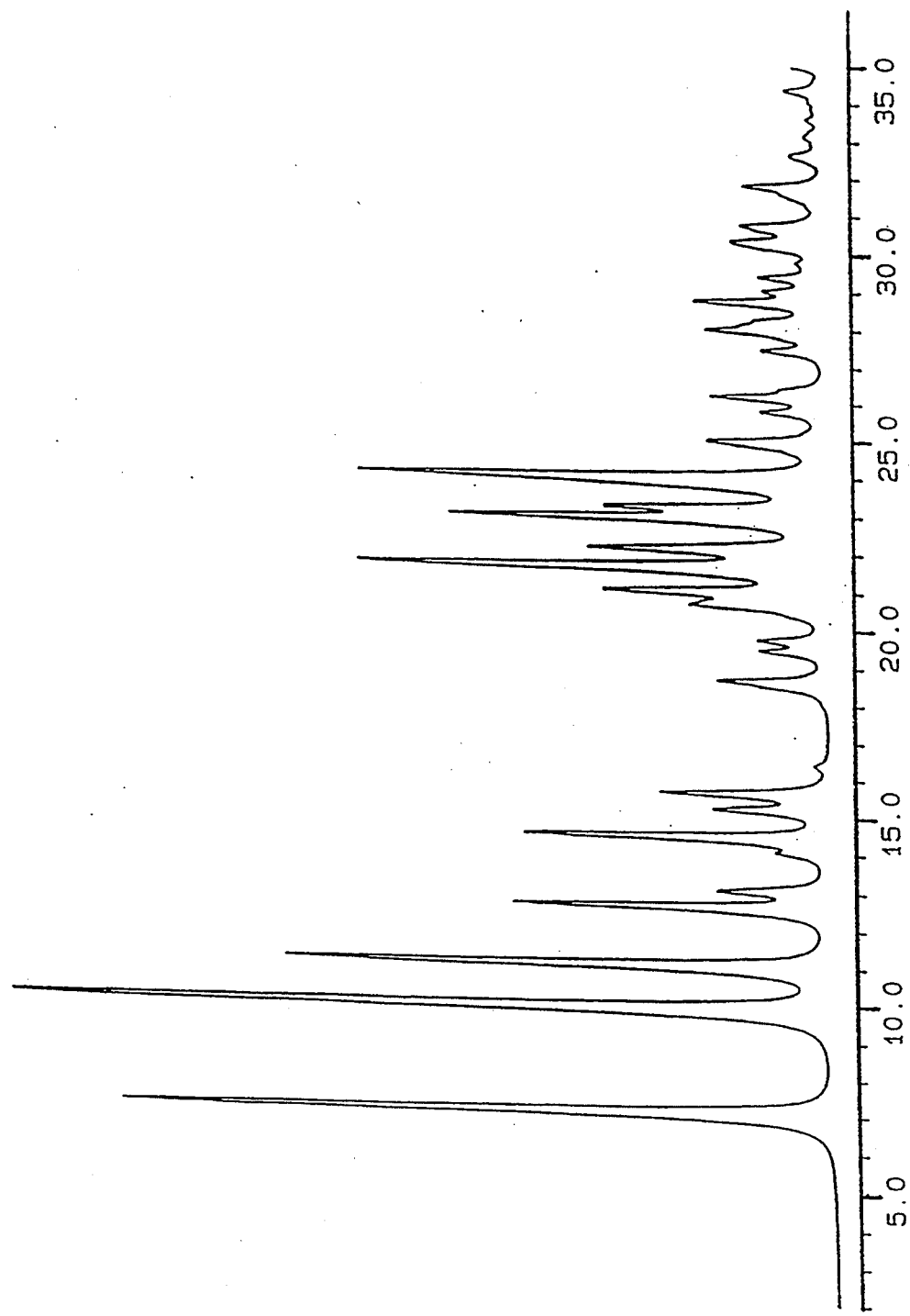
FIGS. 1a, 1b, 1c, and 1d show, respectively, the powder X-ray diffraction pattern, the $^{13}$C nuclear magnetic resonance spectrum, the infrared spectrum, and the differential scanning calorimetric thermogram of the prior art non-solvated Form I crystalline polymorph of 1-(4-amino-6,7-dimethoxy-2-quinazolinyl)-4-(tetrahydro-2-furoyl)piperazine monohydrochloride.
Figure 1B:
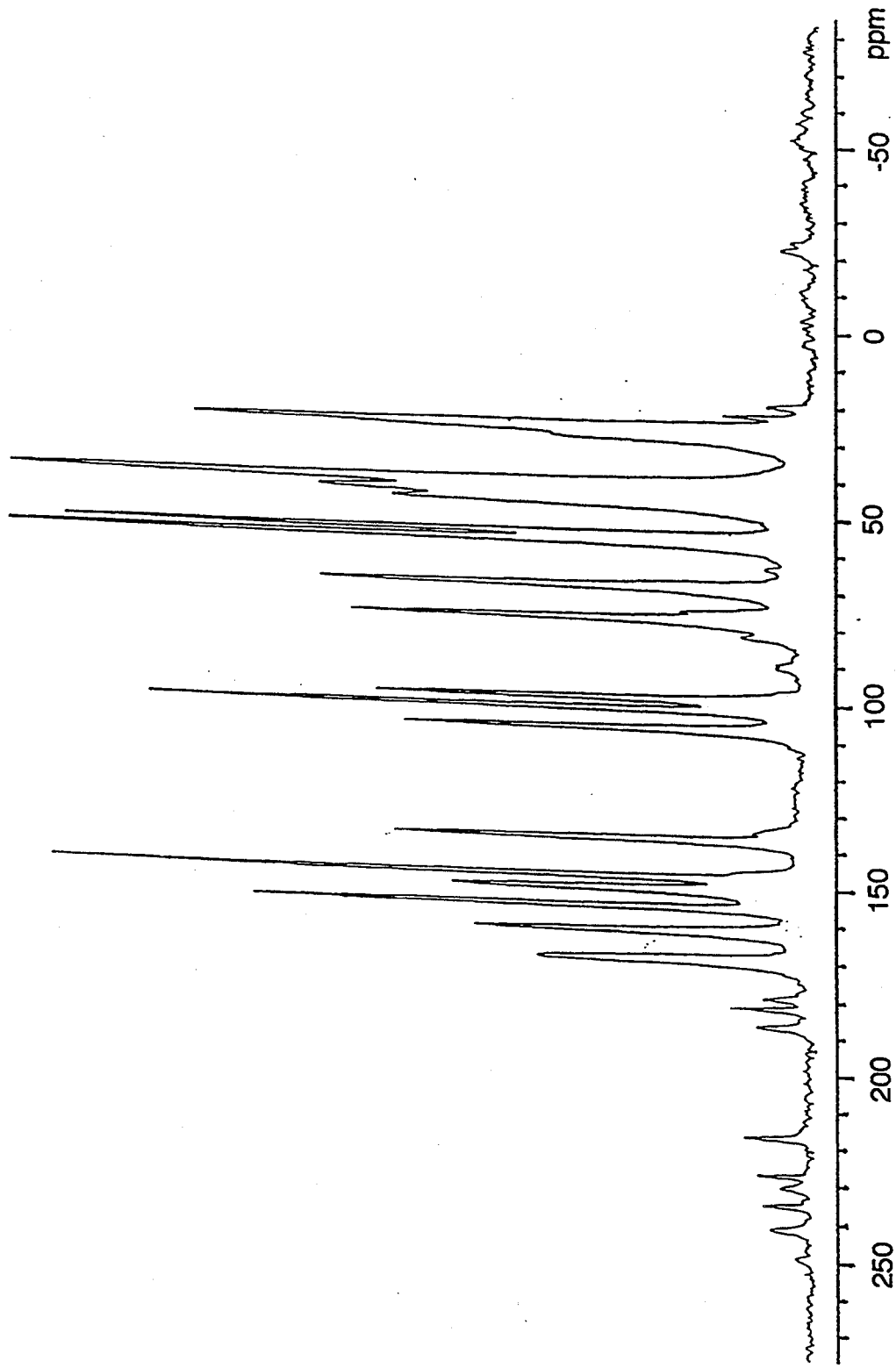
Figure 1C:
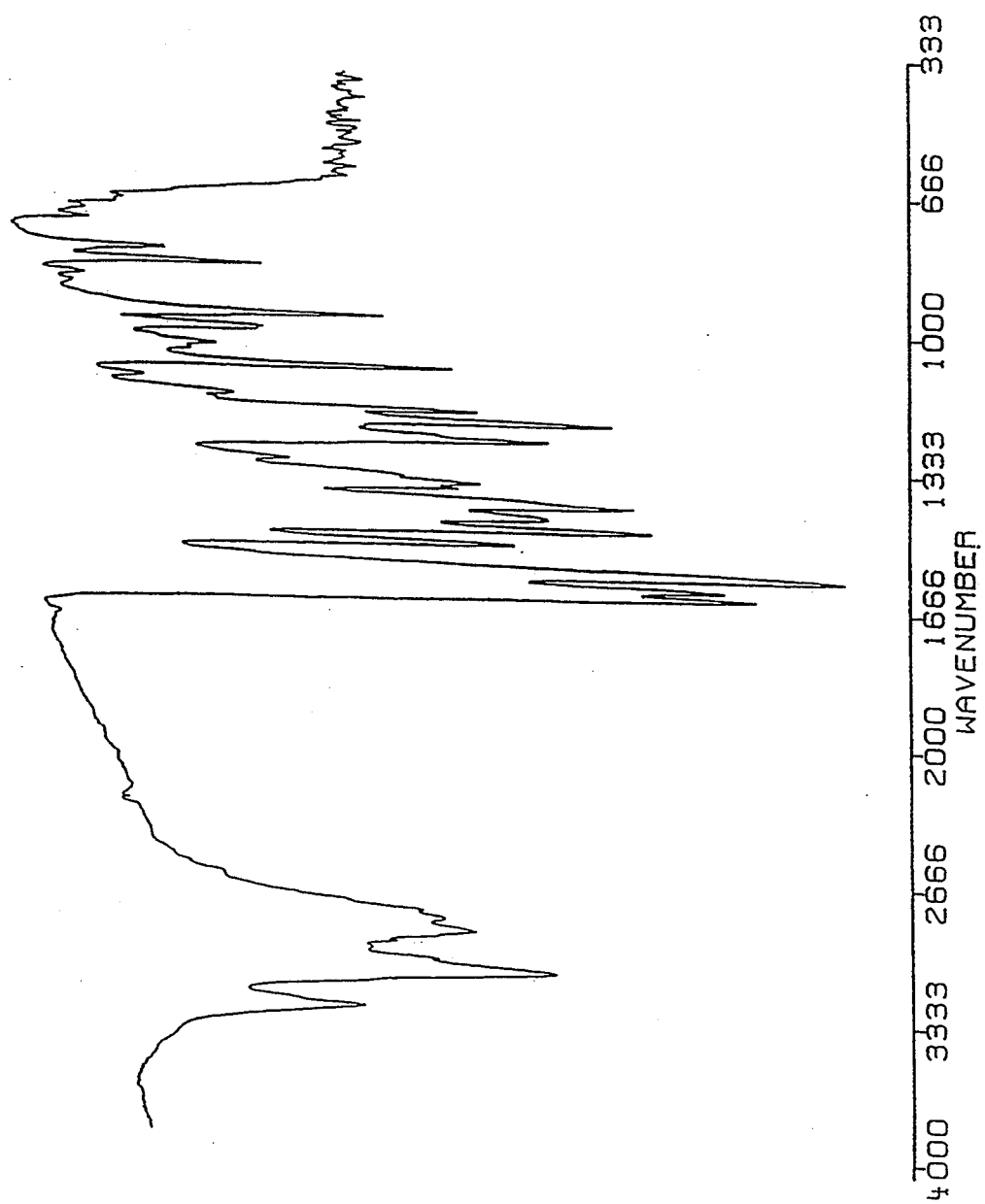
Figure 1D:
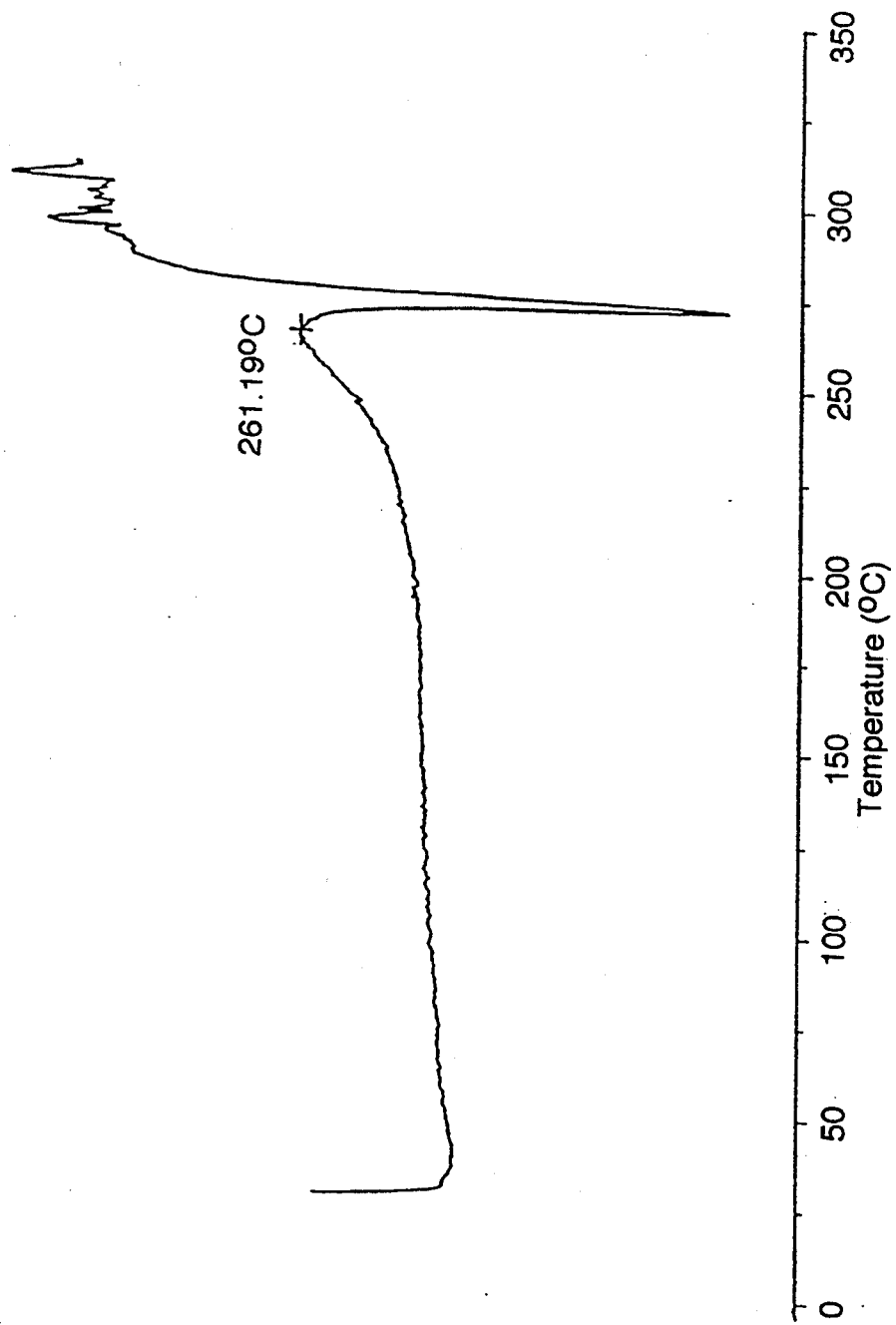
Figure 2A:
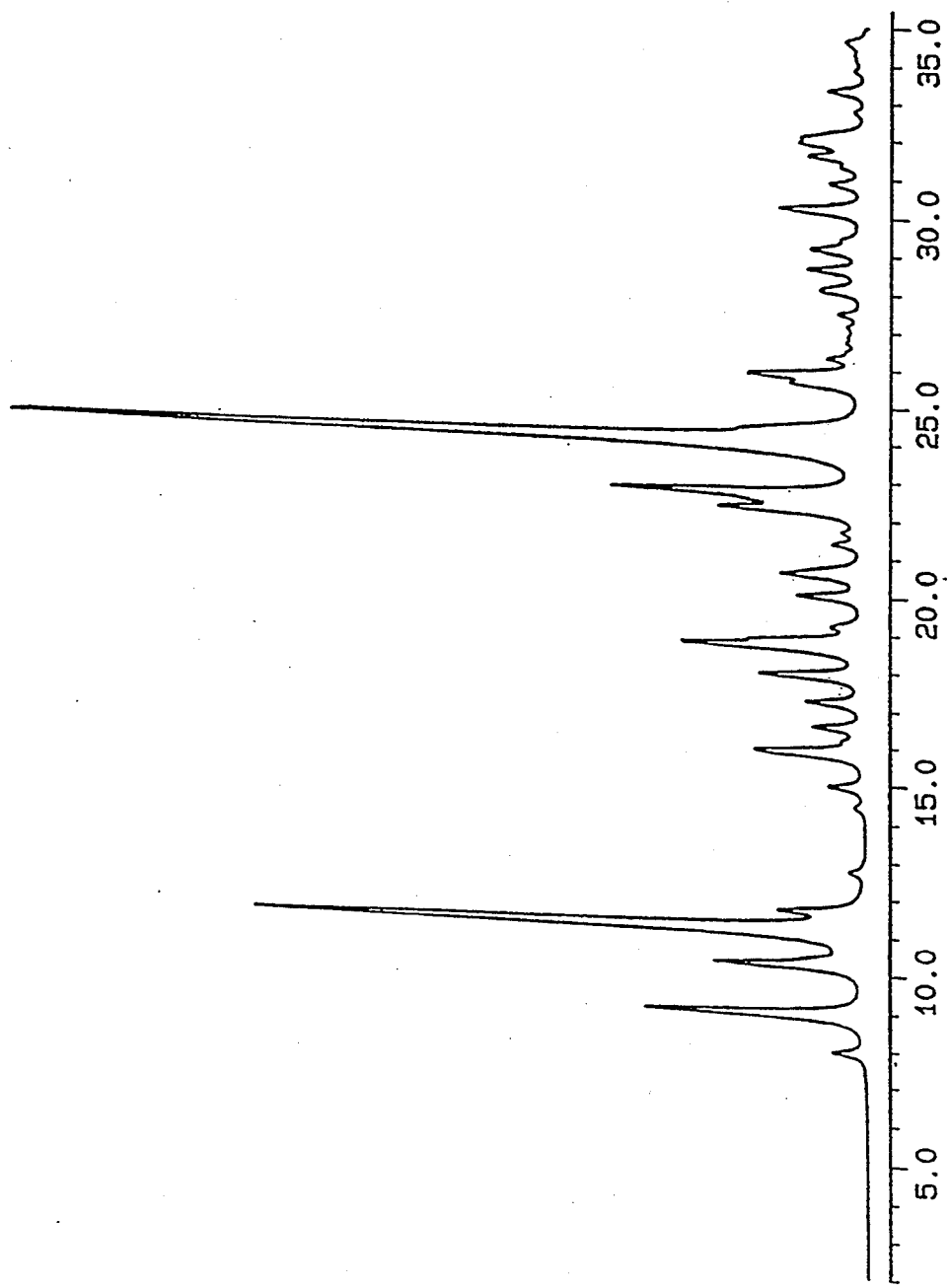
FIGS. 2a, 2b, 2c, and 2d show, respectively, the powder X-ray diffraction pattern, the $^{13}$C nuclear magnetic resonance spectrum, the infrared spectrum, and the differential scanning calorimetric thermogram of the prior art dihydrate crystalline form of 1-(4-amino-6,7-dimethoxy-2-quinazolinyl)-4-(tetrahydro-2-furoyl)piperazine monohydrochloride.
Figure 2B:
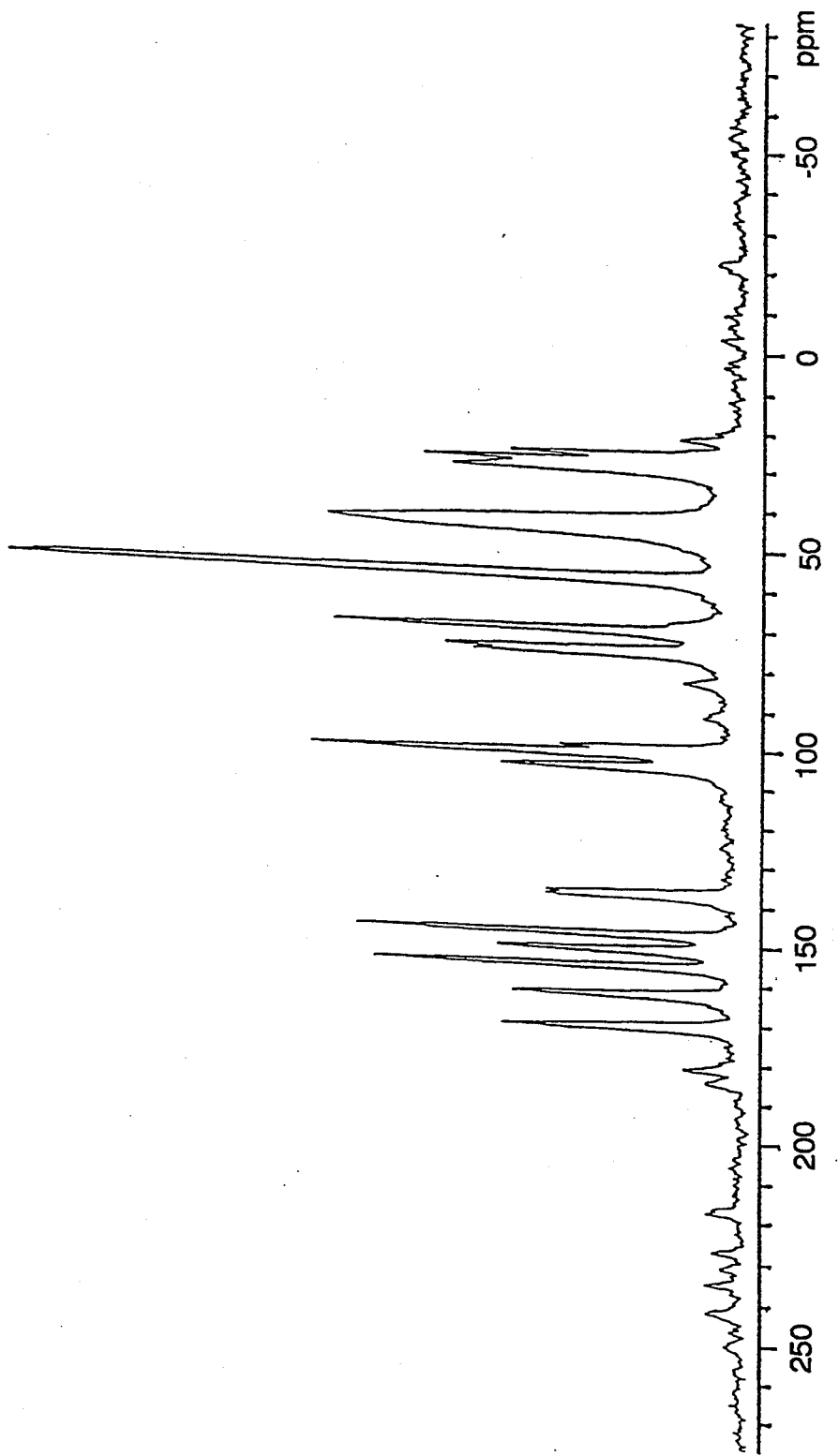
Figure 2C:
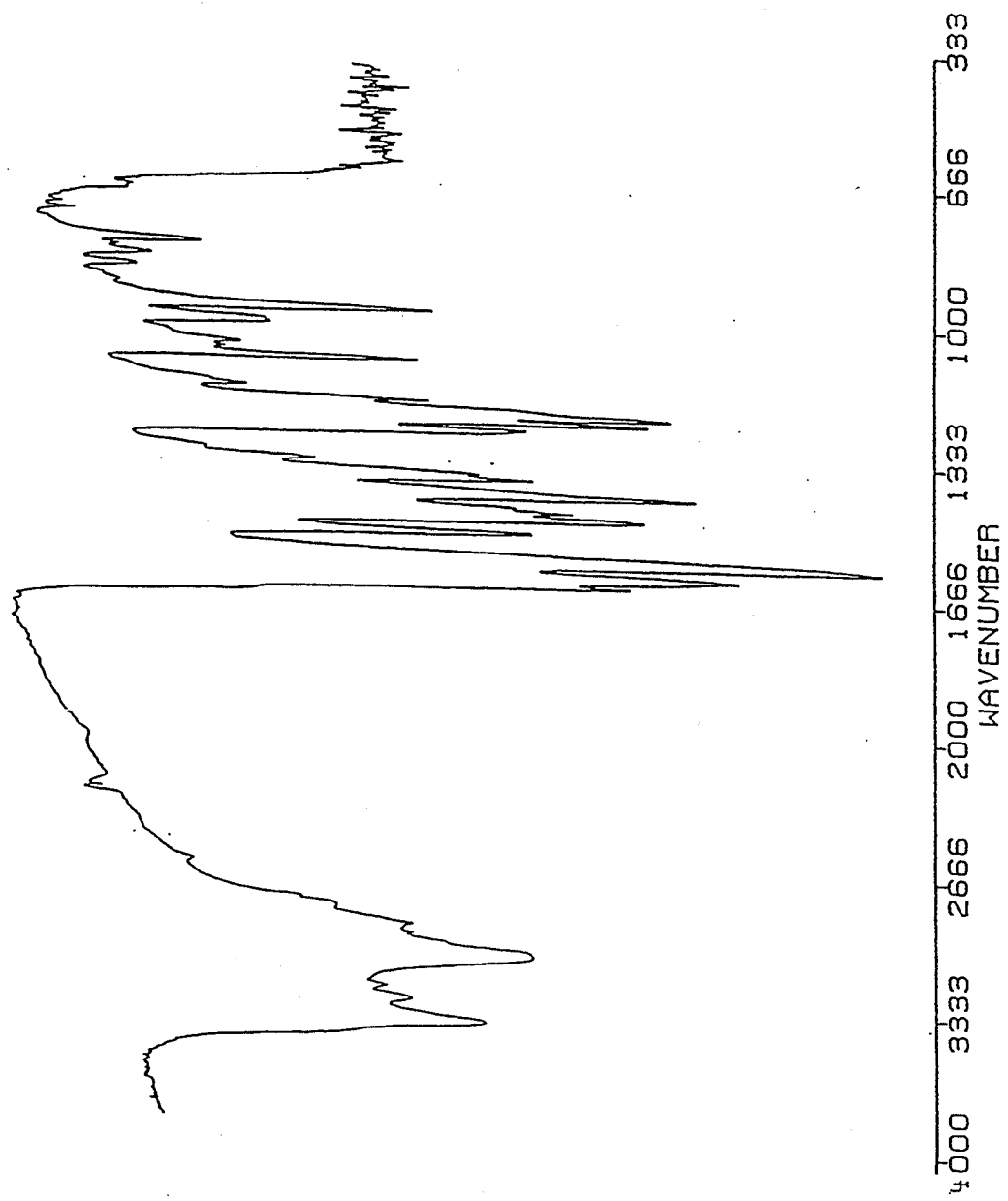
Figure 2D:
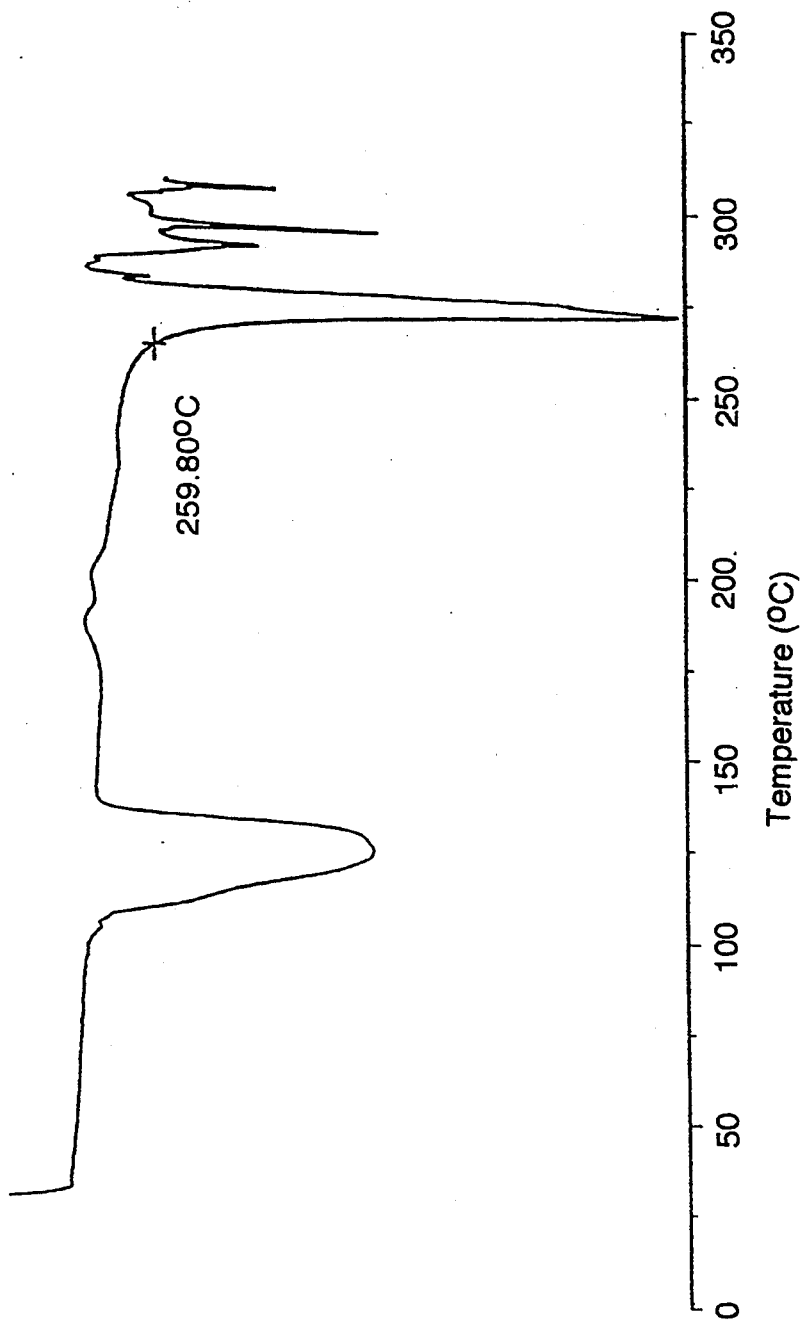
Figure 3A:
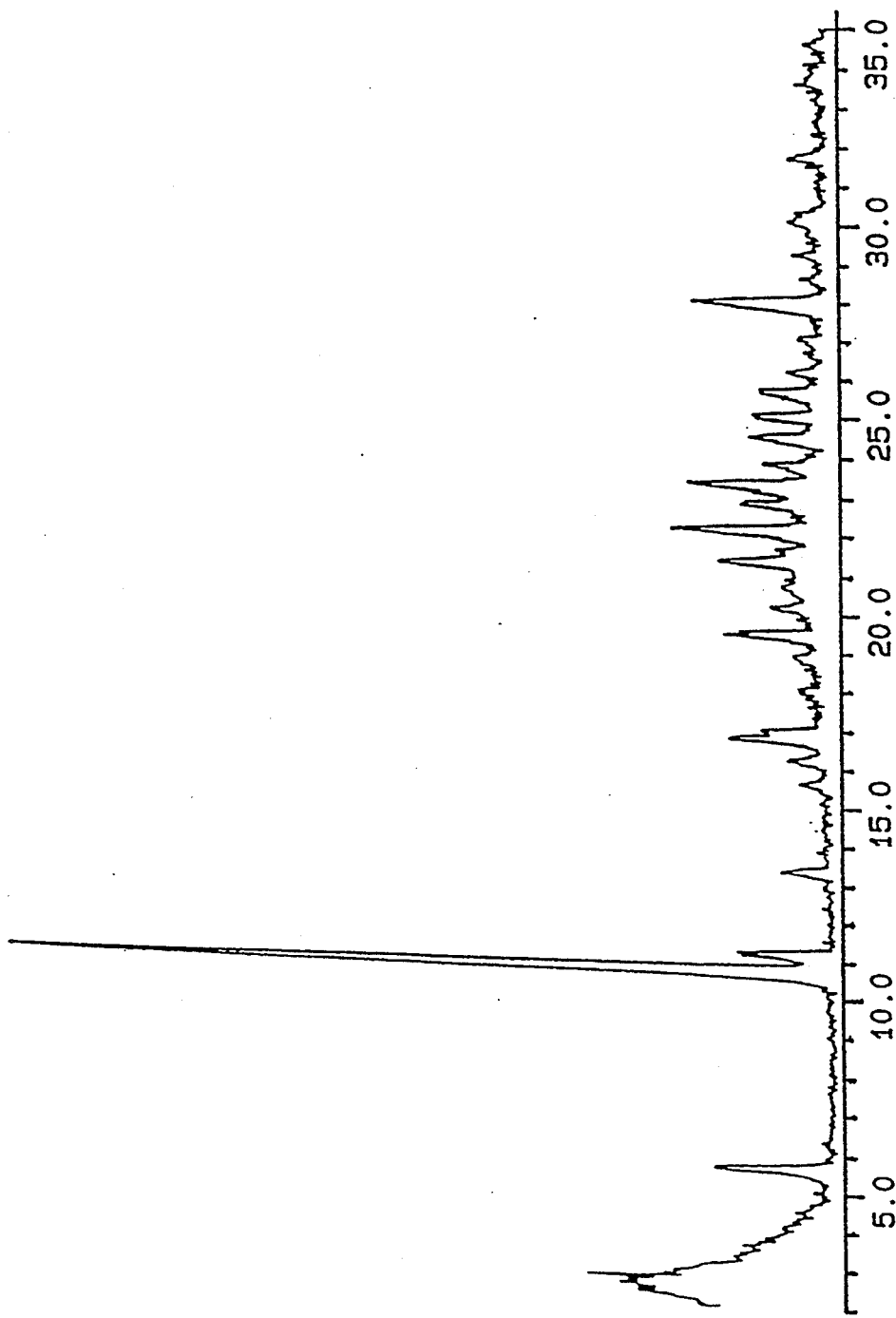
FIGS. 3a, 3b, 3c, and 3d show, respectively, the powder X-ray diffraction pattern, the $^{13}$C nuclear magnetic resonance spectrum, the infrared spectrum, and the differential scanning calorimetric thermogram of the non-solvated Form II crystalline polymorph of 1-(4-amino-6,7-dimethoxy-2-quinazolinyl)-4-(tetrahydro-2-furoyl)piperazine monohydrochloride.
Figure 3B:
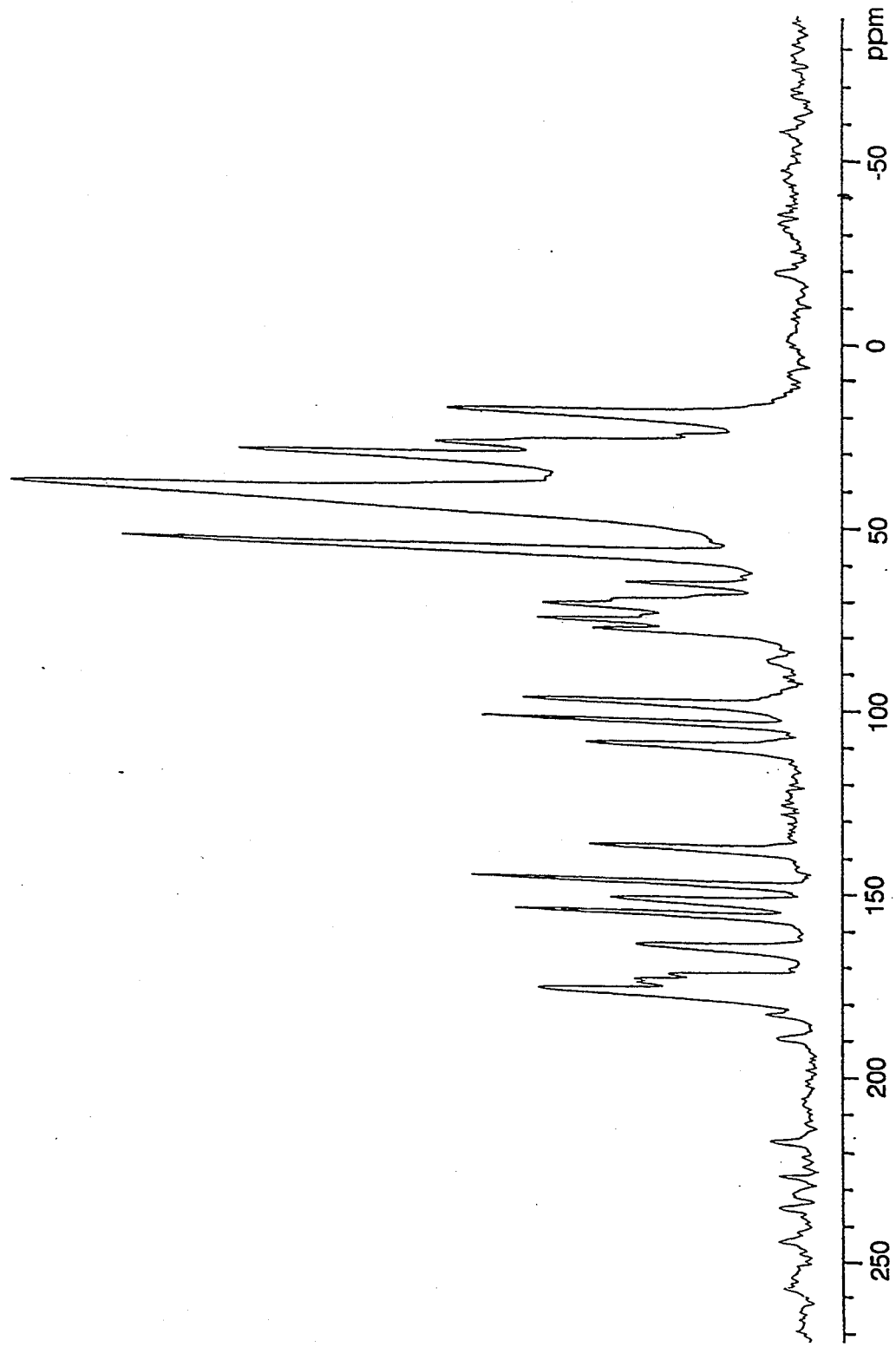
Figure 3C:
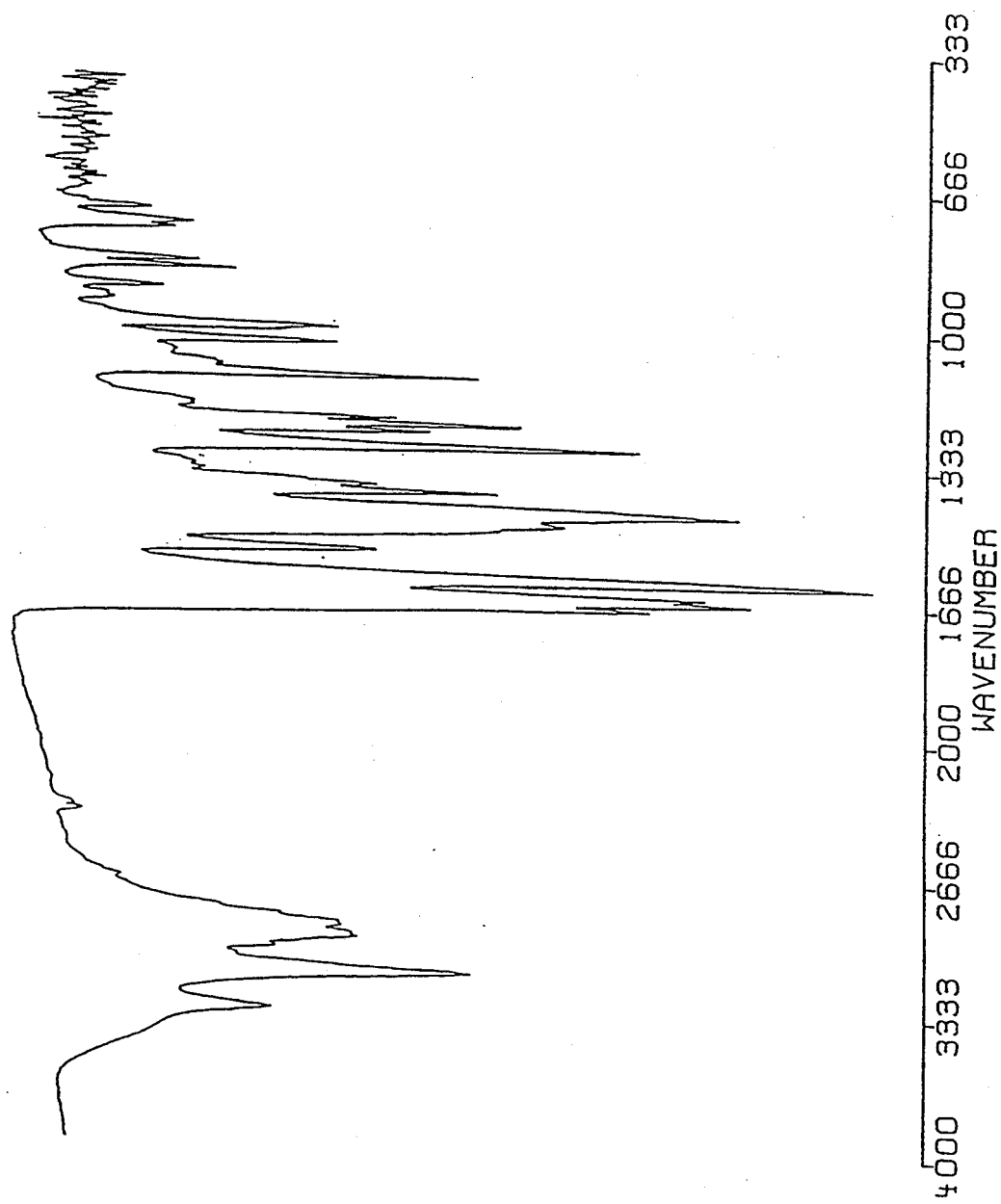
Figure 3D:
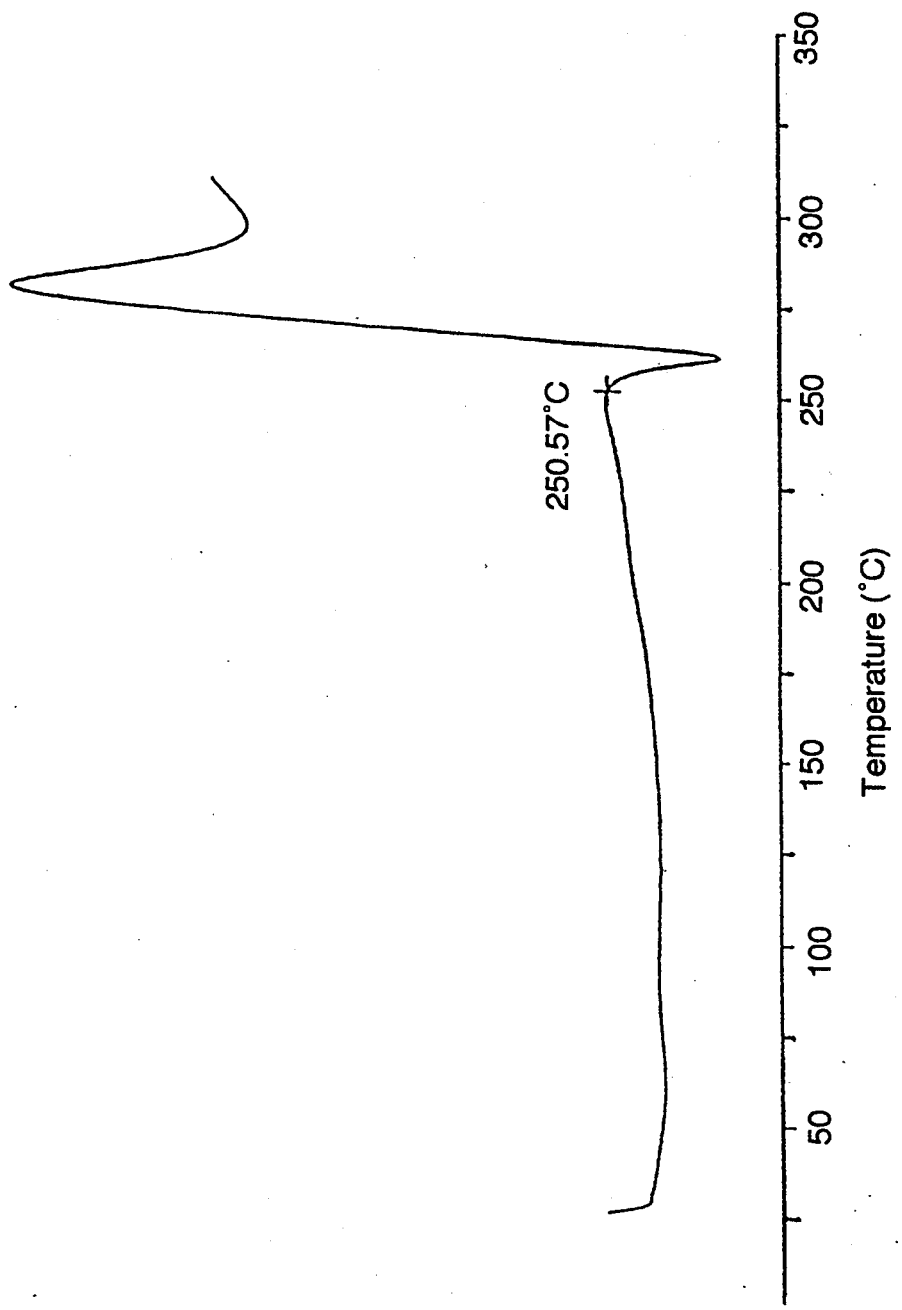

The present invention provides, in its principle embodiment, a novel, non-solvated crystalline polymorph of the compound 1-(4-amino-6,7-dimethoxy-2-quinazolinyl)-4-(tetrahydro-2-furoyl)piperazine monohydrochloride ("terazosin monohydrochloride"). For the sake of identification, this material is designated the "Form III" crystalline polymorph throughout this specification and the appended claims. This crystalline polymorph rapidly dissolves in water and is the non-solvated form of terazosin monohydrochloride most easily prepared in both high purity and high yield.

In another embodiment, the present invention provides the compound 1-(4amino-6,7-dimethoxy-2-quinazolinyl)-4-(tetrahydro-2-furoyl)piperazine monohydrochloride methanolate which is useful as an intermediate in the production of non-solvated crystalline forms and the dihydmate form of terazosin monohydrochloride.

In other embodiments of this invention there are provided processes for making both the Form III crystalline polymorph of terazosin and the methanolate intermediate, as well as methods for the conversion of the methanolate intermediate to the non-solvated crystalline polymorphs of terazosin.

DETAILED DESCRIPTION 1-(4-Amino-6,7-dimethoxy-2-quinazolinyl )-4-(tetrahydro-2-furoyl)piperazine monohydrochlofide (also known by its generic name, "terazosin" monohydrochlofide) exists in several forms including an amorphous form, two non-solvated crystalline forms (Forms I and II) and a dihydrate crystalline form.

The term "non-solvated" as used throughout this specification and the appended claims in reference to terazosin and its salts (particularly the hydrochloride salt) mean crystalline polymorphs of the salt which are substantially free of solvent which comprises an integral part of the crystalline structure of the solid.

U.S. Pat. No. 4,026,894 discloses in Example VI a method for preparing a non-solvated crystalline modification of terazosin monohydrochloride, termed "Form I" throughout this specification and the appended claims. The powder X-ray diffraction pattern, $^{13}C$ nuclear magnetic resonance spectrum, infrared spectrum, and the differential scanning calorimetric thermogram of Form I of terazosin monohydrochloride are presented in FIGS. 1a–1d.

Terazosin monohydrochloride dihydrate and its preparation are disclosed in U.S. Pat. No. 4,251,532, and the material is characterized by the spectral data shown in FIGS. 2a–2d.

U.S. Pat. No. 5,294,615 discloses a non-solvated crystalline polymorph of terazosin monohydrochloride which is distinct from Form I referred to above and is termed "Form II" throughout this specification and the appended claims. The crystalline Form II is characterized by the data which are presented in FIGS. 3a–3d.

It has been found, in accordance with the present invention, that there exists yet another non-solvated crystalline polymorph of terazosin monohydrochloride which is distinct from both the Form I and Form II crystalline polymorphs mentioned above. This latter polymorph is designated throughout this specification and the appended claims "Form III." It has also been found that, under appropriate conditions, an isolable methanolate of terazosin monohydrochloride can be prepared which is useful as an intermediate leading to any of the polymorphs of non-solvated terazosin monohydrochloride, Forms I–III and the dihydrate. The methanolate can be readily prepared in good yield from the free base. The methanolate thus prepared is essentially free from acidic contamination.

Terazosin has the structure:

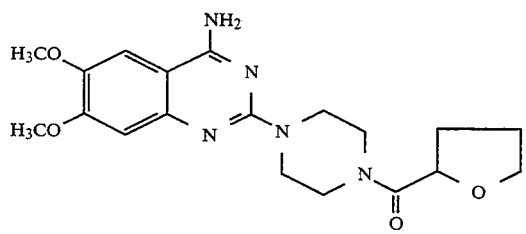

and possesses a basic amine function at position 4 of the quinazoline ring. The free base form of terazosin does not possess the requisite solubility for convenient oral administration as a therapeutic agent and like most such compounds is converted to the hydrochloride salt for incorporation into oral dosage forms. The usual procedure in the pharmaceutical formulating arts for the preparation of hydrochloride salts of compounds having a basic amine functionality is the reaction of the free amine with an aqueous solution of hydrogen chloride, i.e. dilute hydrochloric acid. In such preparations, if the hydrochloride salt precipitates from the resulting aqueous solution, it is collected by filtration and subsequently purified, usually by recrystallization. If the desired hydrochloride salt does not precipitate from solution, the aqueous solution of the hydrochloride salt is typically lyophilized to produce the solid salt which likewise may be further purified by recrystallization.

This procedure requires several processing steps which are time consuming, costly, and permit extended contact of the therapeutic agent with acidic solutions. Moreover, lyophilization of the aqueous solution of the hydrochloride salt can concentrate any residual excess hydrochloric acid, subjecting the material to potential degradation during its isolation unless special care is taken to insure that there is little or no excess hydrochloric acid remaining in the solution prior to lyophilization.

In the particular case of terazosin, when the parent compound or its hydrochloride salt is in contact for extended periods with aqueous acid, it undergoes an undesirable side reaction which cleaves the compound into its constituent parts:

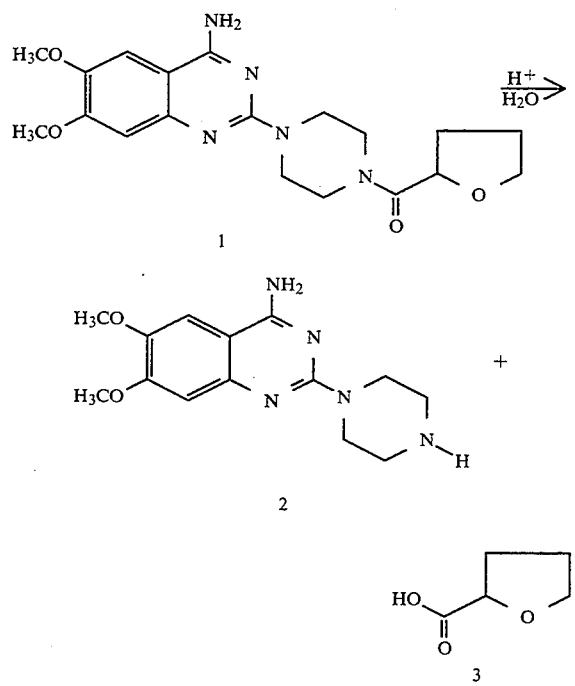

The acidic cleavage of terazosin, 1, into 4-amino-6,7-dimethoxy-2-piperazinylquinazoline, 2, and 2-furoic acid, 3, illustrated in the reaction above occurs rapidly in aqueous medium. Moreover, if the hydrochloride salt is prepared by lyophilization of the reaction mixture of terazosin free base and hydrochloric acid, unless care is taken to remove any excess acid present in the isolated salt, the solid may also contain small amounts of acid which causes degradative cleavage over time.

Thus, the production of terazosin hydrochloride by the conventional method of reacting the free amine base with aqueous hydrochloric acid requires careful attention to the amount of acid employed in the process and the maintenance of short contact times with the acid.

It has been found in accordance with the present invention that an isolable methanolate of terazosin monohydrochloride can be obtained without the need for the use of aqueous hydrochloric acid solutions with its attendant potential for undesirable degradation of either the parent compound during salt formation or the resulting salt. The methanolate is prepared under conditions which minimizes the amount of excess hydrogen chloride in the reaction mixture. The product terazosin monohydrochloride methanolate is readily purified by recrystallization from dry methanol, and can be obtained in high purity and high yield from terazosin free base.

Terazosin monohydrochloride methanolate can be prepared by either direct production from terazosin free base as shown below in Examples 1 and 2 or by conversion of the dihydrate monohydrochloride (as shown by Example 3) or conversion of Form I (Example 4). If the dihydrate monohydrochloride is used as the starting material, the methanolate monohydrochloride is obtained by dissolving the dihydrate in hot methanol followed by precipitation of the desired methanolate by treating the methanol solution with a second dry solvent which is miscible with methanol, typically acetone. Because it is possible to prepare terazosin monohydrochloride methanolate in higher purity by direct reaction of the free base with hydrogen chloride in methanol rather than by conversion of the previously-formed dihydrate, terazosin monohydrochloride methanolate is preferably prepared directly from the free base by suspending terazosin free base in dry methanol and adding a saturated solution of hydrogen chloride gas in an alcohol or mixture of alcohols of two to six carbon atoms until all of the suspended solids dissolve. The alcoholic solution of hydrogen chloride gas is prepared by first drying the alcohol or alcohol mixture by one of the methods detailed below, followed by bubbling dry gaseous hydrogen chloride through the dried alcohol or alcohol mixture until a saturated solution is obtained. The preferred alcohol for preparing the alcoholic hydrogen chloride solution is methanol.

Once the suspended solids have dissolved, addition of the saturated alcoholic solution of hydrogen chloride is stopped and the solvents are removed under vacuum. The advantage of this method is that removal of the methanol and other alcohol(s) under vacuum also minimizes the amount of hydrogen chloride which remains in the mixture during the process of isolating the solid salt. The product of this process is then further purified, if desired or needed, by recrystallization from dry methanol.

Figure 5A:
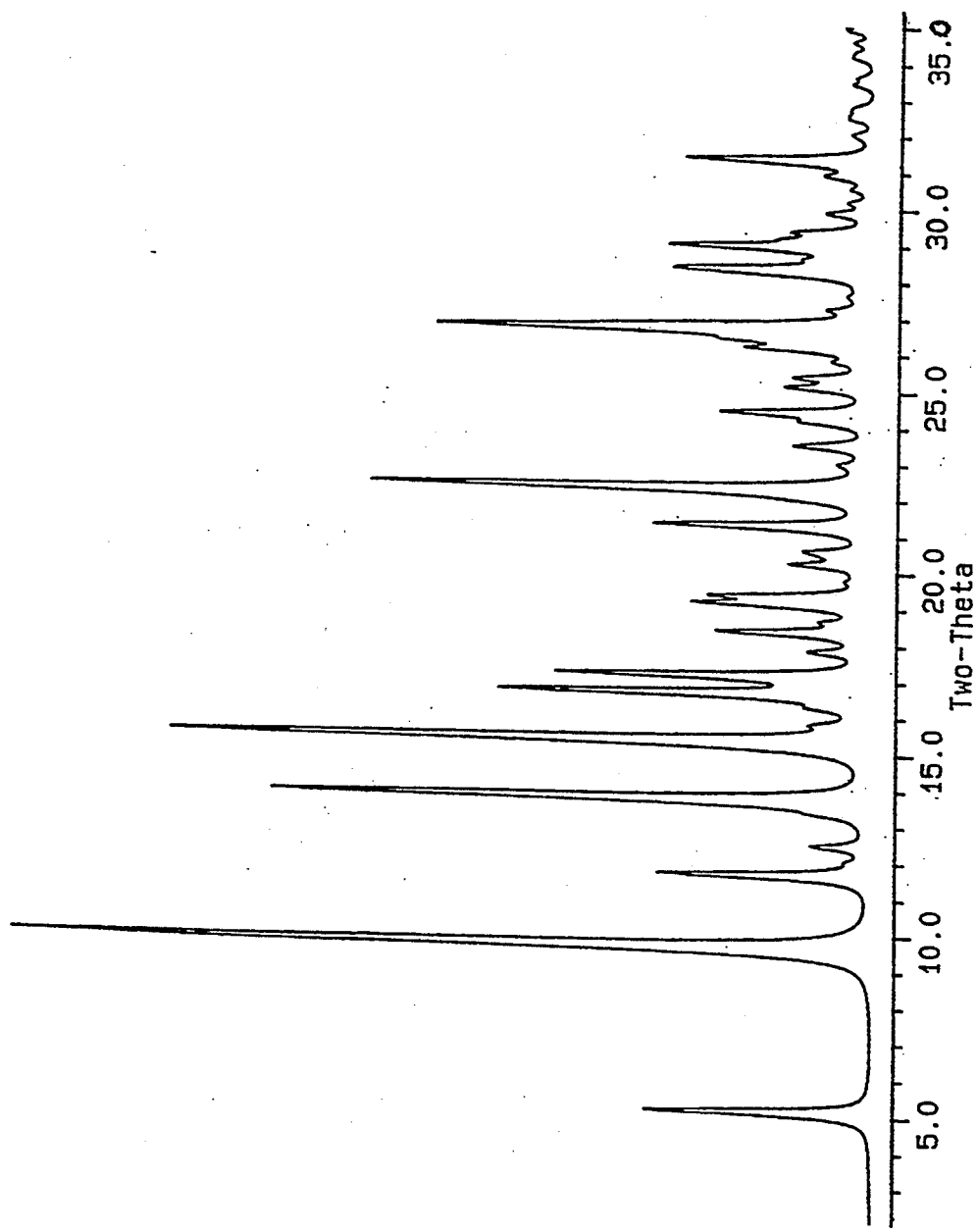
FIGS. 5a, 5b, 5c, and 5d show, respectively, the powder X-ray diffraction pattern, the $^{13}$C nuclear magnetic resonance spectrum, the infrared spectrum, and the differential scanning calorimetric thermogram of 1-(4-amino-6,7-dimethoxy-2-quinazolinyl)-4-(tetrahydro-2-furoyl)piperazine monohydrochloride methanolate of the present invention.
Figure 5B:
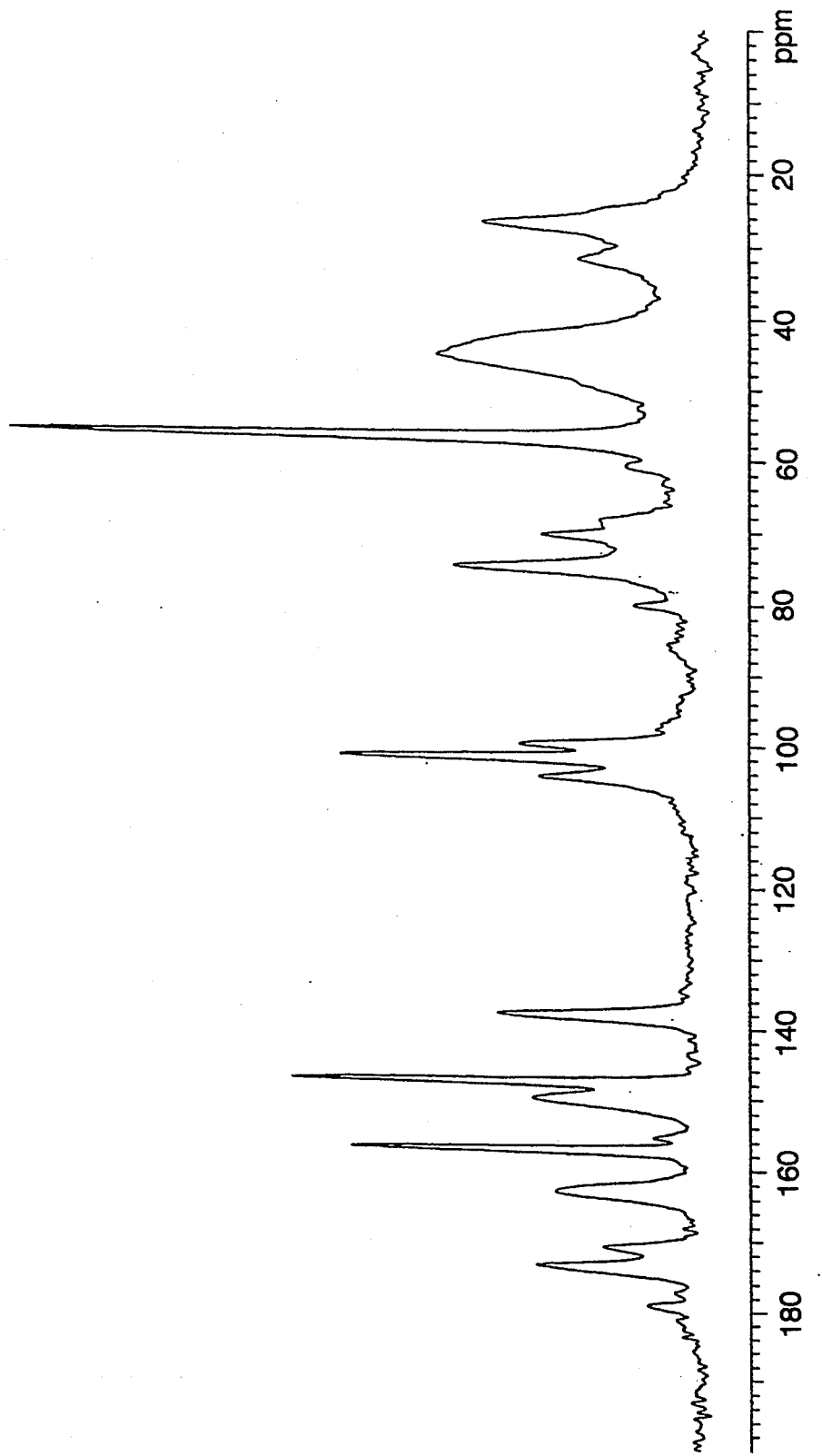
Figure 5C:
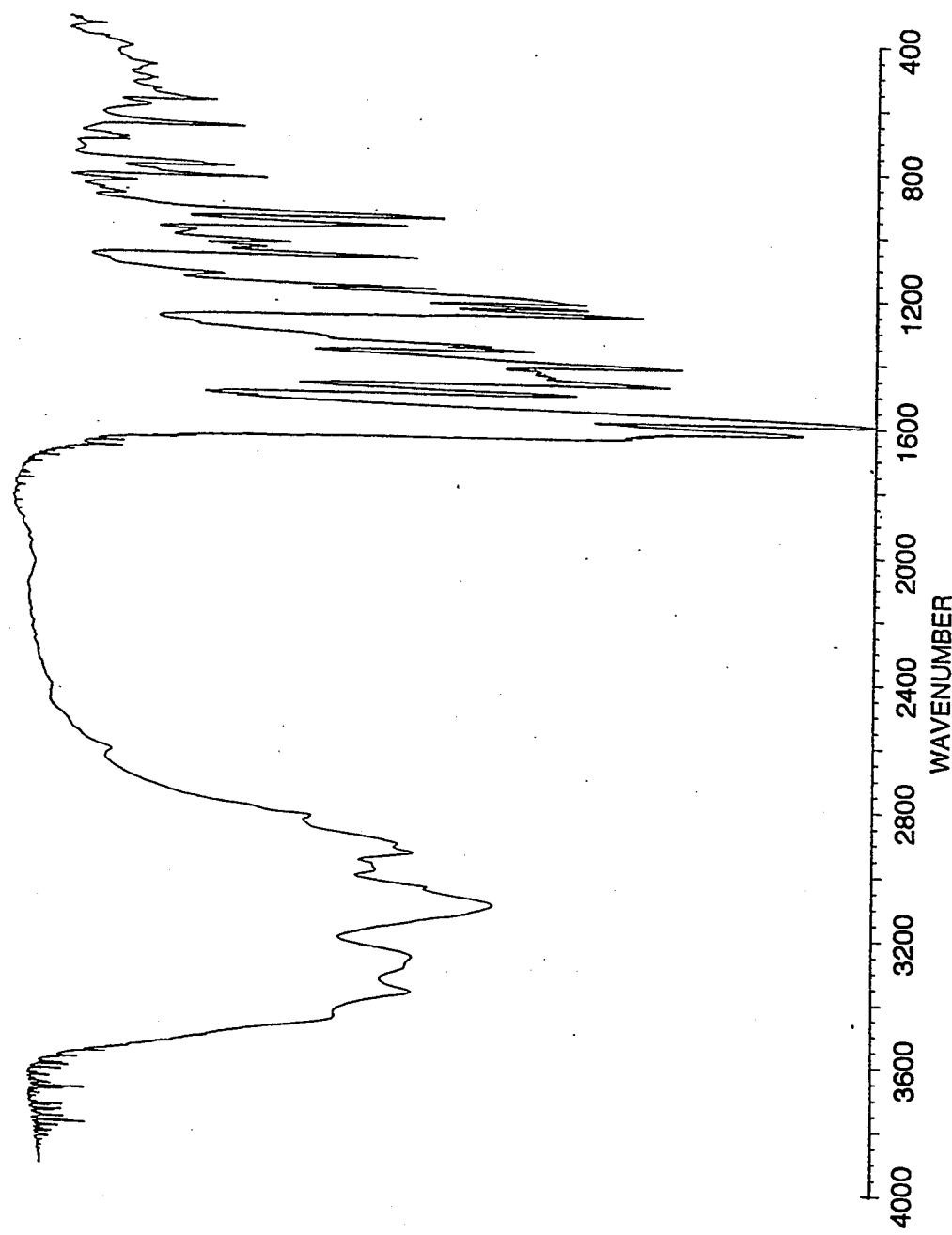
Figure 5D:
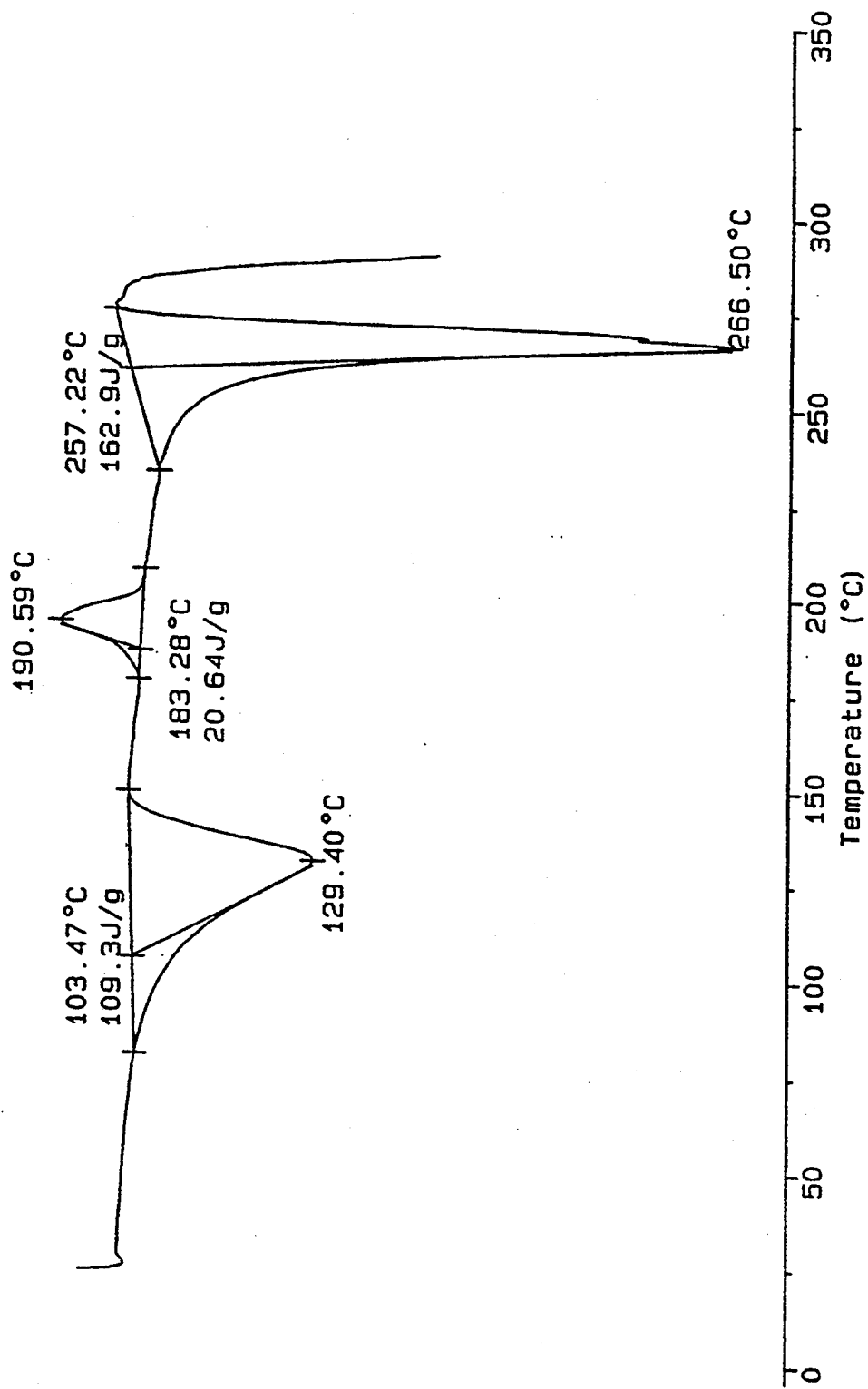

Terazosin monohydrochloride methanolate has one mol of methanol of solvation per mol of terazosin hydrochloride in the crystalline solid. It has the powder X-ray diffraction pattern, $^{13}C$ nuclear magnetic resonance spectrum, infrared spectrum, and the differential scanning calorimetric thermogram which appear in FIGS. 5a–5d herein below. In the differential scanning thermogram of the methanolate shown in FIG. 5d, there can be seen an endotherm peaking at 129.4° C. which is believed to be due to loss of methanol from the crystal and a smaller exotherm peaking at 190.6° C. which is believed to be due to a phase transition. The two-theta angle positions of the peaks in the powder x-ray diffraction pattern of terazosin monohydrochloride methanolate shown in FIG. 5a are 5.09°±0.2°; 9.63°±0.2°; 11.64°35 0.2°; 15.32°±0.2°; 16.63°±0.2°; 21.25°±0.2°; 22.24°±0.2°; 22.28°±0.2°; 26.62°±0.2°; and 28.93°±0.2°.

As shown in Examples 5-10 below, terazosin monohydrochloride methanolate is a useful intermediate which can be readily converted to terazosin monohydrochloride dihydrate or any of the various non-solvated crystalline polymorphs of terazosin monohydrochloride (i.e., Forms I, II and III). Because the monohydrochloride methanolate can be prepared with a high degree of purity, it thus provides a route for the preparation of these other forms of the monohydrochloride which are also quite pure.

Terazosin monohydrochloride methanolate is readily converted to the non-solvated crystalline forms of terazosin monohydrochloride by contacting the monohydrochloride methanolate with a $C_2$–$C_6$ alcohol, $C_3$–$C_6$ ketone or mixture thereof. The method of contacting may be either by slurrying the methanolate in the solvent or solvent mixture at ambient temperature for an extended period or at a higher temperature, typically about 50° C. for a period of time sufficient to remove the methanol of crystallization, typically for a period several minutes to two hours. A convenient variation of the process comprises heating the monohydrochloride methanolate with the solvent under reflux.

The solvents employed for the process of converting terazosin monohydrochloride methanolate to the other non-solvated crystalline modifications are selected from $C_2$–$C_6$ alcohols, $C_3$–$C_6$ ketones such as acetone, methyl ethyl ketone ("MEK"), diethyl ketone, and alcohols such as ethanol, propanol, isopropanol, n-butanol, sec-butanol, iso-butanol and the like or mixtures of these alcohols and ketones with the ketones being preferred because of the lower solubility of the monohydrochloride in these solvents.

The solvents are carefully dried prior to use by methods well known in the art such as contacting them with dehydrating alumnosilicate or aluminophosphate zeolites, commonly called "molecular sieves." The molecular sieves are chosen from those grades having a pore size which is optimized for trapping water molecules, preferably about 4 Angstrom units. The solvent is allowed to stand at room temperature over the molecular sieves until dry, generally for a period of from about 24 to about 48 hours. An additional drying step may be taken which consists of contacting the molecular sieve-dried solvent with anhydrous magnesium or sodium sulfate or of filtering the molecular sieve-dried solvent through a pad of anhydrous magnesium or sodium sulfate prior to use. The water content of the solvents can be checked by well known methods such as the Karl Fischer method (*Angew. Chem.*, 48:394 (1935); D. Smith, et al., *J. Am. Chem. Soc.*, 6 1:2407 (1939)).

Figure 4A:
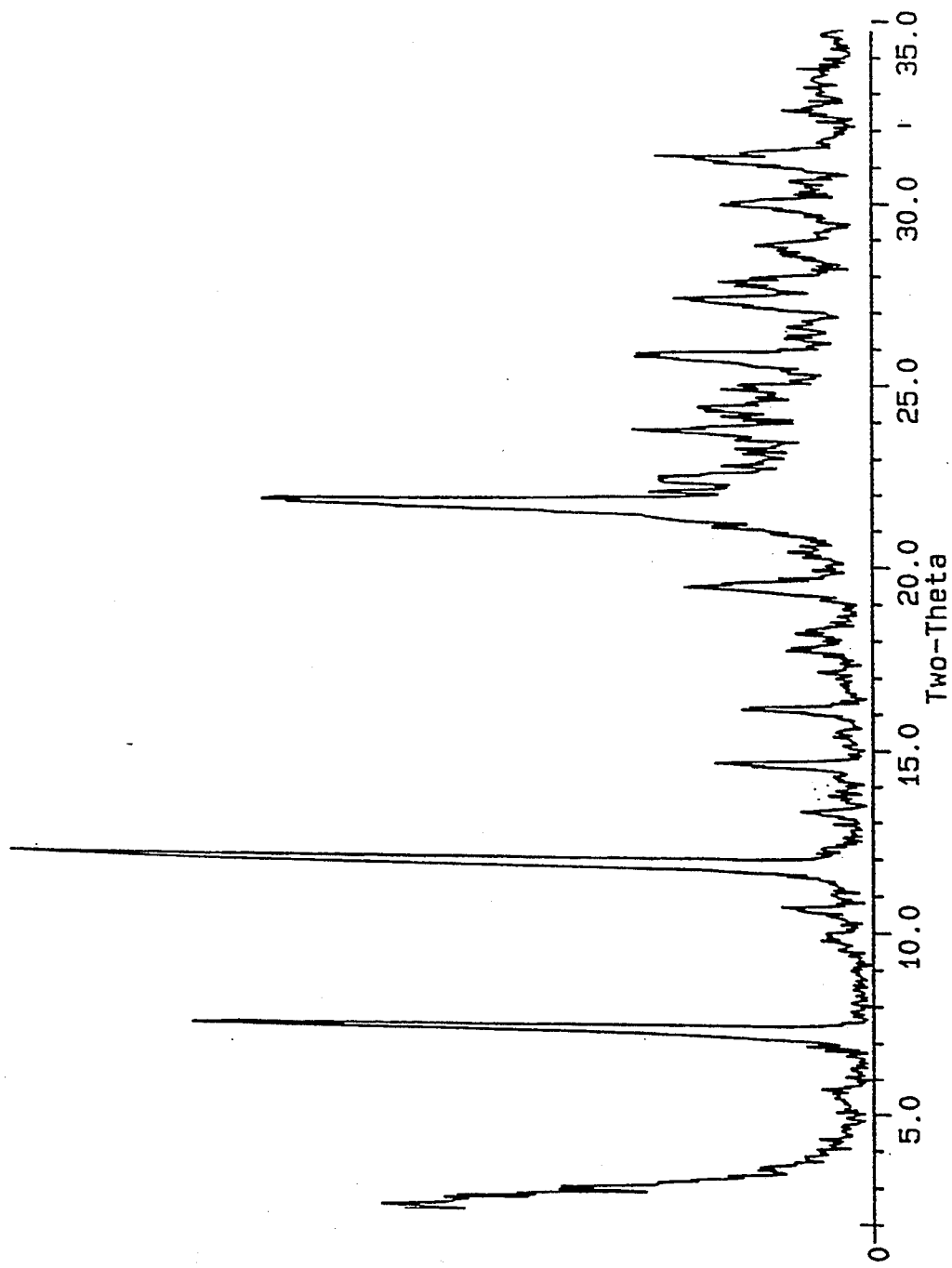
FIGS. 4a, 4b, 4c, and 4d show, respectively, the powder X-ray diffraction pattern, the $^{13}$C nuclear magnetic resonance spectrum, the infrared spectrum, and the differential scanning calorimetric thermogram of the non-solvated Form III crystalline polymorph of 1-(4-amino-6,7-dimethoxy-2-quinazolinyl)-4-(tetmhydro-2-furoyl)piperazine monohydrochloride of the present invention.
Figure 4B:
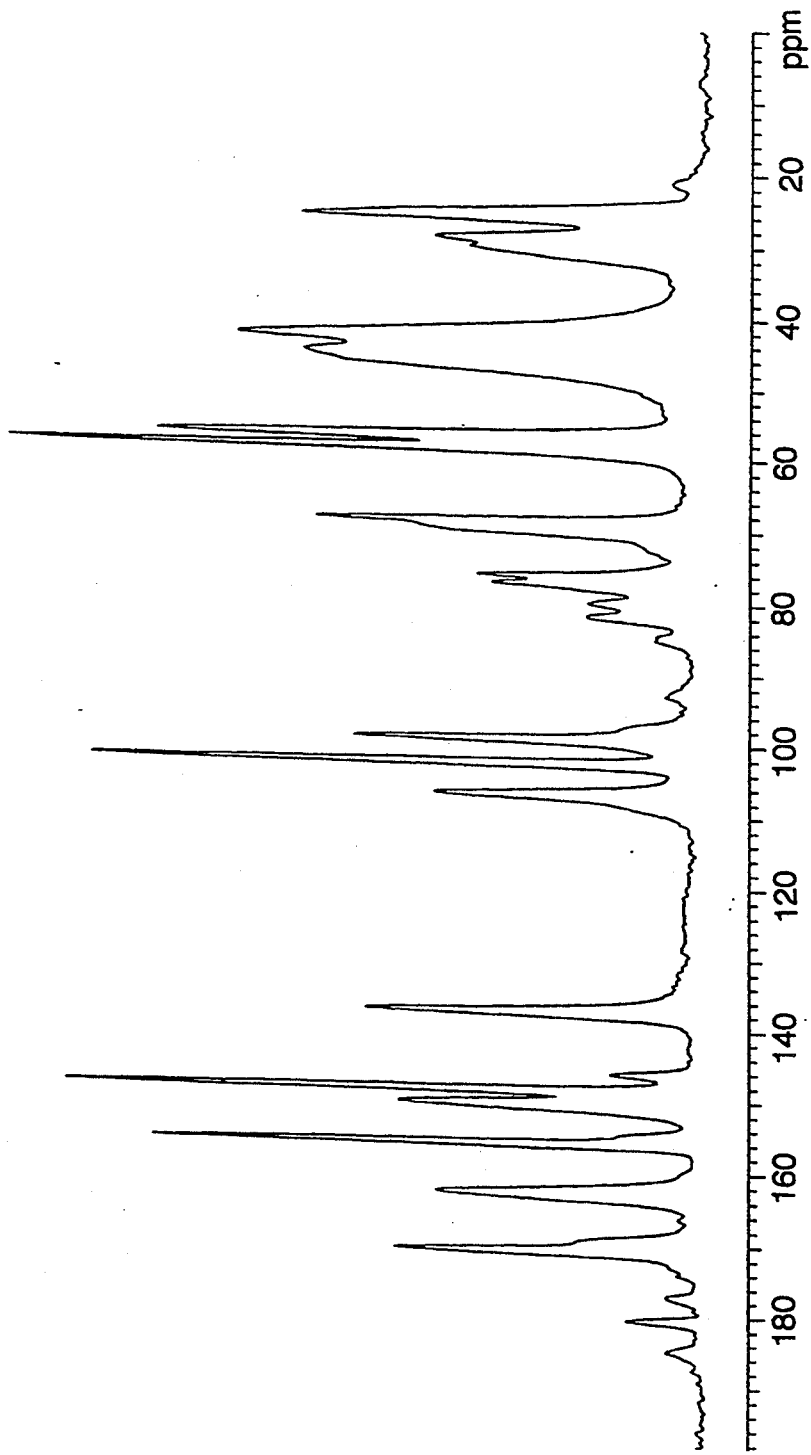
Figure 4C:
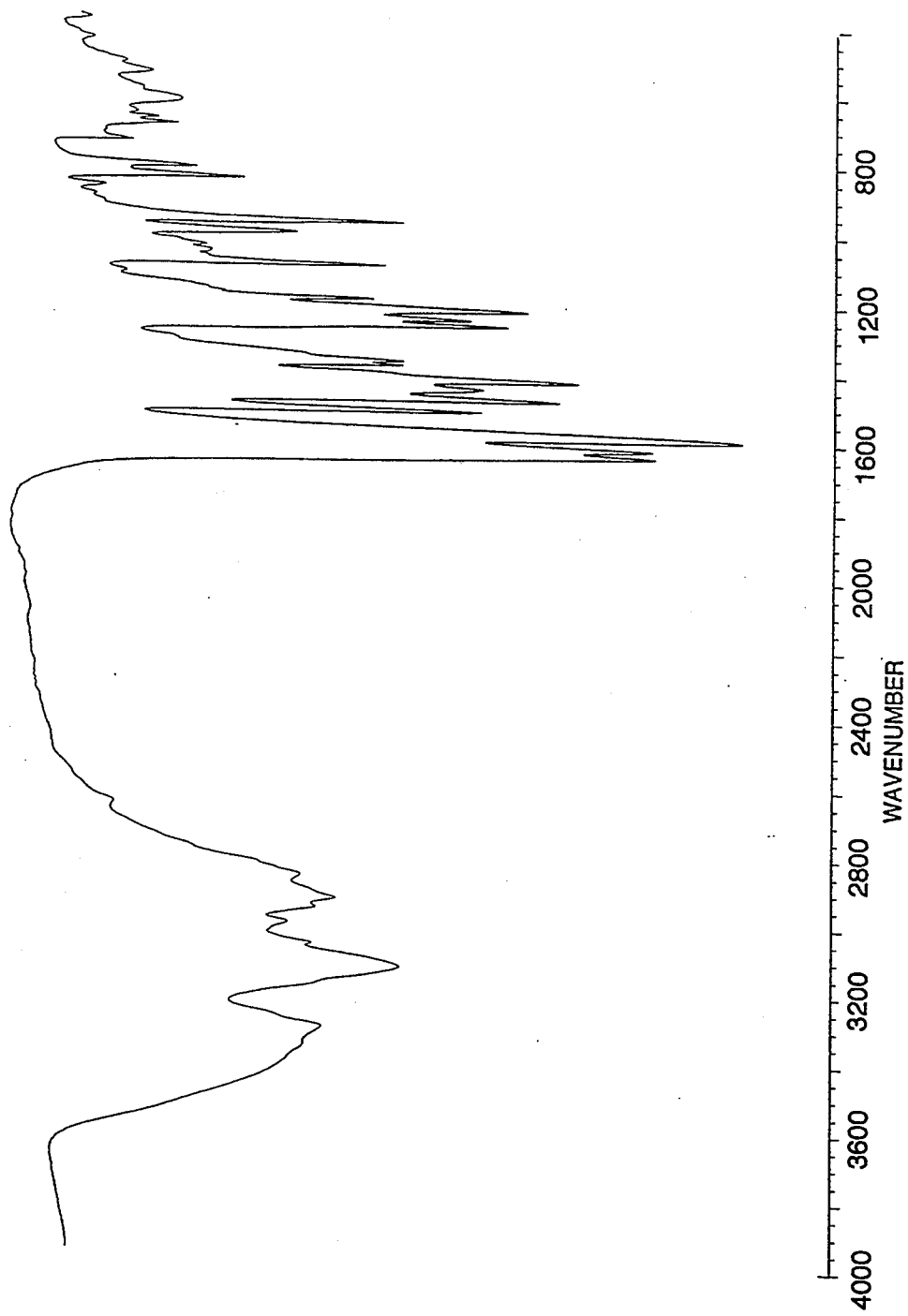
Figure 4D:
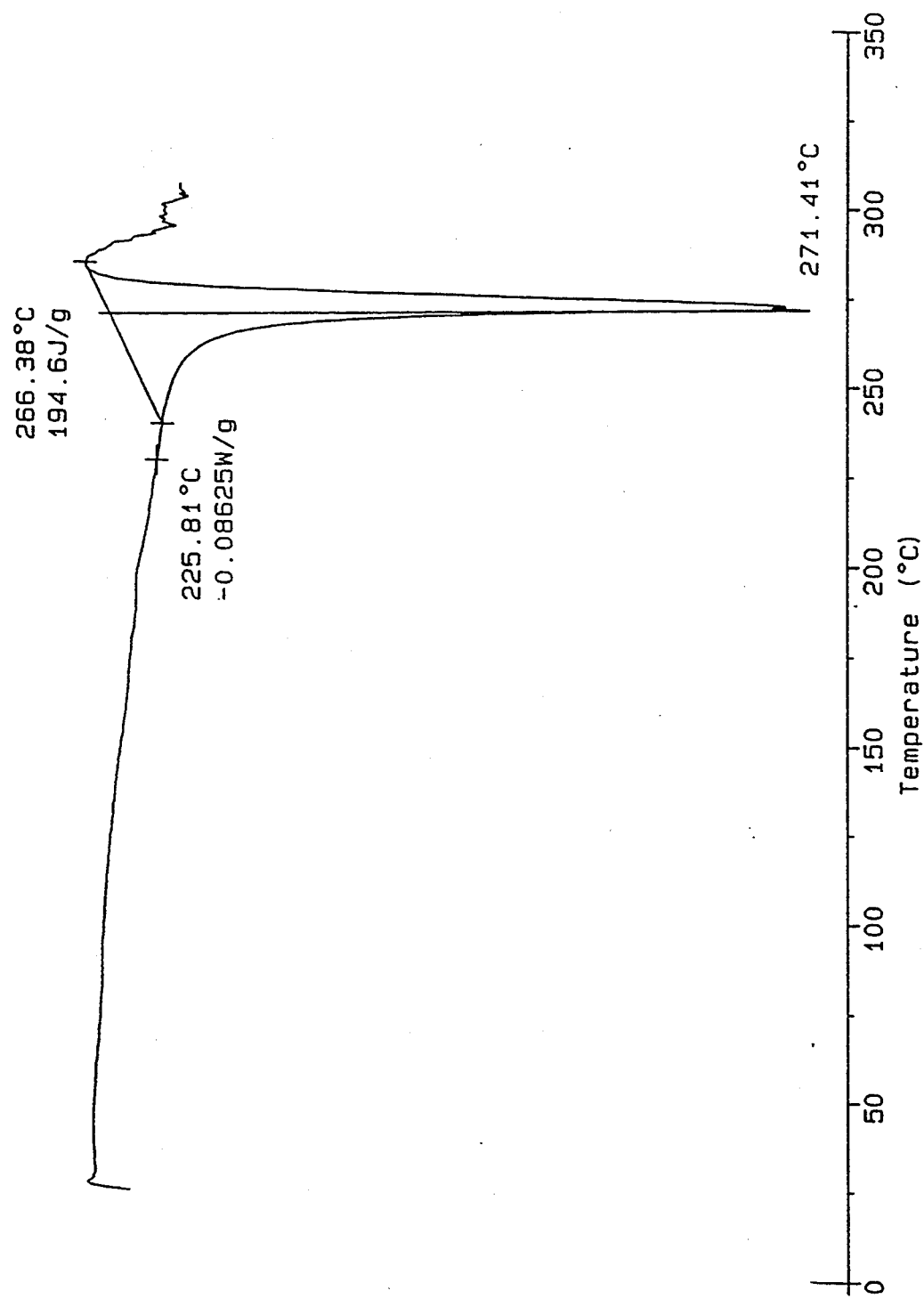

As shown by the processes exemplified by Examples 7-9 below, contacting terazosin monohydrochloride methanolate with a $C_2$–$C_6$ alcohol or $C_3$–$C_6$ ketone or a mixture thereof at a temperature of about 50° C. converts the methanolate to a previously unknown non-solvated crystalline polymorph of terazosin which is distinct from both Forms I and II. The physical data for terazosin monohydrochloride Form III appear in FIGS. 4a–4d. The two-theta angle positions of the peaks in the powder x-ray diffraction pattern of terazosin monohydrochloride Form III shown in FIG. 4a are 7.29°±0.2°; 11.81°±0.2°; 14.59°±0.2°; 19.43°±0.2°; 20.40°±0.2°; 21.61°±0.2°; 22.36°±0.2°; 23.69°±02.20; 24.34°±0.2°; 24.80°±0.2°; 25.75°±0.2°; 27.29°±0.2°; 29.96°±0.2°; and 31.20°±0.2°.

As shown by the data appearing in Table 1 below, this form of terazosin monohydrochloride, like the other non-solvated forms, dissolves in water much more rapidly than the dihydrate form. The data in Table 1 were collected, for each data point, by weighing 2 g samples of terazosin monohydrochloride dihydrate and each of Forms I, II and II of the non-solvated monohydrochloride separately into 50 mL centrifuge tubes. Five mL of distilled water were added to each tube and the tubes shaken for the times indicated and then rapidly filtered through a 0.45 μu nylon membrane filter. The resulting flitrates were serially diluted with water 2 to 10, 5 to 0, 5 to 50, 5 to 50 and 5 to 100 mL and the ultraviolet absorption maximum at 254 nm measured. The concentrations of the dissolved terazosin were then calculated from the absorption data using dam from a series of standard concentrations.

TABLE 1

| Solubility of Various Forms of Terazosin Monohydrochloride (mg/mL) | | | | |
|---|---|---|---|---|
| Time (Minutes) | Form I | Form II | Form III | Dihydrate |
| 0.5 | 273 | 280 | 235 | 29 |
| 1 | 283 | 253 | 237 | 30 |
| 2 | 289 | 311 | 269 | 27 |
| 4 | 276 | 323 | 261 | 26 |

The data show that while a limit of solubility of about 30 mg/mL is rapidly reached for terazosin monohydrochloride dihydrate, solubilities of about ten times that amount can be rapidly achieved with the non-solvated forms of terazosin monohydrochloride, including the Form III. Of the various non-solvated forms of terazosin hydrochloride, however, Form III is most readily produced from the methanolate in good yield as shown by the Examples presented below. For example, when prepared from the methanolate by treatment with a ketone (acetone in Example 7 or methyl ethyl ketone in Example 9) the yield of the non-solvated hydrochloride Form III is in excess of 95%.

Parenteral delivery systems are known comprising dual chamber syringes in which the therapeutic compound to be delivered is in a dry powdered form in a first chamber of the syringe, initially separate from sterile aqueous saline solution in a second chamber. Just prior to administration, the contents of the two chambers are mixed and the drug is dissolved. The non-solvated forms of terazosin monohydrochloride are best suited for this type of delivery system because of the rapidity with which they can be dissolved in water. Of the various non-solvated forms of terazosin monohydrochloride, Form III is most readily producible in high purity and yield through the methanolate intermediate. It is thus the non-solvated form of terazosin monohydrochloride of choice for parenteral dosage forms where purity is critical.

The following examples are provided to enable one skilled in the art to practice the present invention, but should not be read as limiting the scope of the invention as it is defined by the appended claims.

Examples 1–4: Preparation of Terazosin Monohydrochloride Methanolate

EXAMPLE 1

Prepration of Crystalline Terazosin Monohydrochloride Methanolate—From Terazosin Base (Method I)

A solution of hydrogen chloride in methanol was prepared by bubbling the gas through dry methanol for several minutes. 1-(4-Amino-6,7-dimethoxy-2-quinazolinyl)-4-(tetrahydro-2-furoyl)piperazine (1.2 g, 3.1 mmol) was placed in an Erlenmeyer flask, together with a magnetic stirring bar, and the methanolic solution of hydrogen chloride was added until the solid had completely dissolved (about 13 mL). After the resulting mixture had stood at about 25° C. for several minutes, a precipitate formed. The mixture was cooled in an ice bath for thirty minutes and the precipitated solid collected by filtration to yield 1.1 g (2.41 mmol, 77.8%) of 1-(4-amino-6,7-dimethoxy-2-quinazolinyl)-4-( tetrahydro-2-furoyl)piperazine monohydrochloride methanolate.

EXAMPLE 2

Preparation of Crystalline Terazosin Monohydrochloride Methanolate—From Terazosin Base (Method II)

A saturated solution of hydrogen chloride in isopropyl alcohol was added dropwise to a suspension of 1.18 g (3.1 mmol) of 1-(4-amino-6,7-dimethoxy-2-quinazolinyl)-4-(tetrahydro-2-furoyl)pipemzine in 100 mL of dry methanol until the suspended solids had completely dissolved. The solvent was then removed under vacuum to yield 1.32 g (2.9 mmol, 93.4%) of 1-(4-amino-6,7-dimethoxy-2-quinazolin)-4-(tetrahydro-2-furoyl)piperazine monohydrochloride methanolate.

EXAMPLE 3

Preparation of Crystalline Terazosin Monohydrochloride Methanolate—From Terazosin Monohydrochloride Dihydrate 1-(4-Amino-6,7-dimethoxy-2-quinazolinyl)-4-(tetrahydro-2-furoyl)piperazine monohydrochloride dihydrate (7.37. g, 16.0 mmol, prepared in accordance with the teachings of U.S. Pat. No. 4,25 1,532) was placed in an Edenmeyer flask and dissolved in a minimum amount (about 10 mL) of hot dry methanol. The solid initially dissolved, but soon turned cloudy and a precipitate formed. The precipitate was collected by filtration and washed with a small quantity of dry methanol followed by dry acetone to yield 6.35 g ( 13.9 mmol, 87.0%) of 1-(4-amino-6,7-dimethoxy-2-quinazolinyl)-4-( tetrahydro-2-furoyl)piperazine monohydrochloride methanolate.

EXAMPLE 4

Preparation of Terazosin Monohydrochloride Methanolate from Tergosin Monohydrochloride (Form I)

Terazosin monohydrochloride (Form I, 5.3 g, 12.5 mmol) was dissolved in a minimum of hot methanol which had been previously dried over molecular seives. Acetone was added to a point where the solution developed cloudiness, and the mixture was allowed to stand approximately four days undisturbed. The white solid which precipitated was collected by vacuum filtration and washed with dry acetone to yield 3.6 g (7.90 mmol, 63%) of terazosin monohydrochloride methanolate.

Examples 5–10: Conversion of Terazosin Monohydrochloride Methanolate to Other Forms of Terazosin Monohydrochloride

EXAMPLE 5

Preparation of Terazosin Monohydrochloride (Form I) from Terazosin Monohydrochloride Methanolate Terazosin monohydrochloride methanolate (1.06 g, 23 mmol) was dissolved in approximately 10 mL of hot absolute ethanol in a 250 mL Edenmeyer flask. The solution was slowly cooled to ambient temperature and allowed to stand undisturbed overnight. The precipitated solids were collected by vacuum filtration on a Buchner funnel and washed with dry acetone to yield 0.76 g (1.8 mmol, 77.9%) of terazosin monohydrochlo-

EXAMPLE 6

Preparation of Teraosin Monohydrochloride (Form II) from Terazosin Monohydrochloride Methanolate To a 100 mL round-bottom flask containing 0.760 g (1.7 mmol) of terazosin monohydrochloride methanolate were added 25 mL of absolute ethanol. The flask was fitted with a reflux condenser and the slurry was heated under reflux for approximately 24 hours. The mixture was cooled and the precipitated solids collected to yield 0.390 g (0.92 mmol, 54.1%) of terazosin monohydrochloride which was shown by its powder x-ray diffraction pattern to conform to the non-solvated Form II crystalline polymorph.

EXAMPLE 7

Preparation of Terazosin Monohydrochloride (Form III) from Terazosin Monohydrochloride Methanolate—Treatment with Acetone To a 250 mL round-bottomed flask containing crystalline 1-(4-amino-6,7-dimethoxy-2-quinazolinyl)-4-(tetrahydro-2-furoyl)piperazine monohydrochloride methanolate (2.1 g, 4.6 mmol) was added 50 mL of dry acetone. The resulting slurry was stirred and heated at 50° C. for ten minutes. Following this treatment, the solution was cooled in an ice bath for thirty minutes after which the precipitated solid was collected by filtration to yield 1.9 g (4.5 mmol, 97.4%) of terazosin monohydrochloride which was shown by its powder x-ray diffraction pattern to conform to the non-solvated Form III crystalline polymorph.

EXAMPLE 8

Preparation of Terazosin Monohydrochloride (Form III) from Teramzosin Monohydrochloride Methanolate—Treatment with Ethanol To a 100 mL round-bottomed flask containing crystalline 1-(4-amino-6,7-dimethoxy-2-quinazolinyl)-4-(tetrahydro-2-furoyl)piperazine monohydrochloride methanolate (1.1 g, 2.4 mmol) was added 50 mL of absolute ethanol. The resulting slurry was stirred and heated at 50° C. for thirty minutes. Following this treatment, the solution was cooled in an ice bath for thirty minutes after which the precipitated solid was collected by filtration to yield 0.66 g (1.6 mmol, 64.8%) of terazosin monohydrochloride which was shown by its powder x-ray diffraction pattern to conform to the non-solvated Form III crystalline polymorph.

EXAMPLE 9

Preparation of Terazosin Monohydrochloride (Form III) from Terazosin Monohydrochloride Methanolate—Treatment with Methyl Ethyl Ketone To a 250 mL round-bottomed flask containing crystalline 1-(4-amino-6,7-dimethoxy-2-quinazolinyl)-4-(tetrahydro-2-furoyl)piperazine monohydrochloride methanolate (2.01 g, 4.4 mmol) was added 50 mL of methyl ethyl ketone (2butane). The resulting slurry was stirred and heated at 50° C. for thirty minutes. Following this treatment, the solution was cooled in an ice bath for thirty minutes after which the precipitated solid was collected by filtration to yield 1.79 g (4.2 mmol, 95.9%) of terazosin monohydrochloride which was shown by its powder x-ray diffraction pattern to conform to the non-solvated Form III crystalline polymorph.

EXAMPLE 10

Preparation of Terazosin Monohydrochloride Dihydrate from Terazosin Monohydrochloride Methanolate Terazosin monohydrochloride methanolate (3.7 g, 8.1 mmol) was added to a 125 mL Erlenmeyer flask and 30 mL of distilled water were added. The resulting mixture was warmed for ten minutes during which time the solids did not completely dissolve. The slurry was stirred overnight and the solids collected by filtration and allowed to air dry for thirty minutes. The product (1.7 g, 3.7 mmol, 45.6%) was found by its powder x-ray diffraction pattern to conform to terazosin monohydrochloride dihydrate.

We claim:

1. The compound having the name 1-(4-amino-6,7-dimethoxy-2-quinazolinyl)-4-(tetrahydro-2-furoyl)piperazine monohydrochloride methanolate characterized by peaks in the powder x-ray diffraction pattern at values of two theta of 5.09°35 0.2°; 9.63°±0.2°; 11.64°±0.2°; 15.32°±0.2°; 16.63°±0.2°; 21.25°±0.2°; 22.24°±0.2°; 22.28°±0.2°; 26.62°±0.2°; and 28.93°±0.2°.

2. The non-solvated crystalline polymorph of 1-(4-amino-6,7-dimethoxy-2-quinazolinyl)-4-(tetrahydro-2-furoyl)piperazine monohydrochloride characterized by peaks in the powder x-ray diffraction pattern at values of two theta of 7.29°±0.2°; 11.81°±0.2°; 14.59°±0.2°; 19.43°±0.2°; 20.40°±0.2°; 21.61°±0.2°; 22.36°±0.2°; 23.69°±0.2°; 24.34°±0.2°; 24.80°±0.20°; 25.75°±0.2°; 27.29°±0.2°; 29.96°±0.2°; and 31.20°±0.2°.

* * * * *

UNITED STATES PATENT AND TRADEMARK OFFICE
CERTIFICATE OF CORRECTION

PATENT NO. : 5,412,095
DATED : May 2, 1995
INVENTOR(S) : James A. Morley, et. al.

It is certified that error appears in the above-indentified patent and that said Letters Patent is hereby corrected as shown below:

Title page, item [75], inventor: Delete "Ramesh F. Patel" and insert-- Ramesh R. Patel--.

Signed and Sealed this

Second Day of January, 1996

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,412,095
DATED : May 2, 1995
INVENTOR(S) : J. A. Morley, et al.

It is certified that error appears in the above-indentified patent and that said Letters Patent is hereby corrected as shown below:

Title page, replace:

"Notice: The portion of the term of this patent subsequent to Mar. 15, 2011 has been disclaimed."

with:

--Notice: The term of this patent shall not extend beyond the expiration date of Pat. No. 5,294,615.--

Signed and Sealed this

Sixth Day of May, 1997

Attest:

BRUCE LEHMAN

Attesting Officer         Commissioner of Patents and Trademarks

UNITED STATES PATENT AND TRADEMARK OFFICE
CERTIFICATE OF CORRECTION

PATENT NO. : 5,412,095
DATED : May 2, 1995
INVENTOR(S) : J.A. Morley *et al.*

It is certified that error appears in the above-identified patent and that said Letters Patent is hereby corrected as shown below:

Column 10, line 41, change "5.09°35" 0.2°"

to --5.09° ± 0.2°--.

Signed and Sealed this

Twenty-third Day of March, 1999

Attest:

Q. TODD DICKINSON

Attesting Officer

Acting Commissioner of Patents and Trademarks